United States Patent [19]

Govindan

[11] Patent Number: 5,493,031
[45] Date of Patent: Feb. 20, 1996

[54] N-HYDROXYSUCCINIMIDE MONOHYDRATE

[75] Inventor: Cheruthur Govindan, Murrysville, Pa.

[73] Assignee: PPG Industries, Inc., Pittsburgh, Pa.

[21] Appl. No.: 260,637

[22] Filed: Jun. 16, 1994

[51] Int. Cl.$^6$ .................................. C07D 207/46
[52] U.S. Cl. ........................... 548/542; 548/545
[58] Field of Search ............................... 548/542

[56] References Cited

U.S. PATENT DOCUMENTS 2,816,111  12/1957  Wegler et al. .................. 260/293.4

FOREIGN PATENT DOCUMENTS

0451519A1  3/1991  European Pat. Off. .
4014272A1  5/1990  Germany .

OTHER PUBLICATIONS

G. W. Anderson et al, "The Use of Esters of N–Hydroxysuccinimide in Peptide Synthesis", J. Am. Chem. Soc., 86, pp. 1838–1842, (1963).

Kirk–Othmer Encyclopedia of Chemical Technology, 2nd ed. (1965), vol. 6, p. 506.

CRC Handbook of Chemistry and Physics, 65th ed. (1984), pp. C–669 thru C–704.

104654y, "Simple synthesis of N–hydroxysuccinimide", Chemical Abstracts, (1967), p. 977.

*Primary Examiner*—David B. Springer
*Attorney, Agent, or Firm*—George D. Morris

[57] ABSTRACT

N-hydroxysuccinimide monohydrate is precipitated from an aqueous solution of N-hydroxysuccinimide. N-hydroxysuccinimide monohydrate is a new compound that can be used to produce anhydrous N-hydroxysuccinimide which is substantially pure. It can also be used as a substitute for N-hydroxysuccinimide when the presence of water is not detrimental.

27 Claims, No Drawings

N-HYDROXYSUCCINIMIDE MONOHYDRATE

N-hydroxysuccinimide [CAS 6066-82-6] ("NHS") and its acylated derivatives, such as for example N-(benzyloxycarbonyloxy)succinimide [CAS 13139-17-8] ("BCS") and N-(9-fluorenylmethoxycarbonyloxy) succinimide [CAS 82911-69-1] ("FCS"), are useful reagents for the synthesis of peptides and antibiotics. NHS is used as an additive to suppress racemization in peptide coupling and for the preparation of active esters. BCS and FCS are used as selective reagents for the introduction of the benzyloxycarbonyl and the 9-fluorenylmethoxycarbonyl protecting groups, respectively, in amino acids and antibiotics.

NHS has heretofore been prepared in anhydrous form by crystallization from organic solvents.

One known method for the preparation of NHS is described in U.S. Pat. No. 2,816,111. According to that method, succinic anhydride [CAS 108-30-5] ("SA") is reacted with free hydroxylamine [CAS 7803-49-8] in methanol. After evaporating the solvent, the product is heated to 160° C. under vacuum for 1½ hours. Extractions and recrystallizations from various organic solvents result in anhydrous N-hydroxysuccinimide as the product.

Anderson, Zimmerman, and Callahan, *Journal of the American Chemical Social*, 86, 1839–1842 (1964) describe the preparation of NHS by the fusion of hydroxylamine hydrochloride [CAS 5470-11-1] and succinic anhydride at 125° C. to 160° C. The reaction product was then worked up with large quantities of various organic solvents to produce anhydrous N-hydroxysuccinimide as the product.

A third method is described in *Chemical Abstracts*, 66, Abstract 104654v (1967). In this method succinic anhydride was reacted with hydroxylamine in a mixed solvent system consisting of water and dioxane. After reaction, the water and dioxane were removed by distillation in vacuum and the residue was heated to 160° C./1.3 kPa until no further water distilled. The residue was then extracted exhaustively with boiling ethyl acetate, the extract was concentrated in vacuum, and the precipitate was recrystallized from ethyl acetate to produce anhydrous N-hydroxysuccinimide.

Employing organic solvents is expensive and requires dealing with the problems of environmentally acceptable handling, use, and disposal. In many cases products obtained by extraction with organic solvents contain succinic acid at about the 2 to 3 percent level.

A new compound, N-hydroxysuccinimide monohydrate, has been discovered that can be used to produce anhydrous N-hydroxysuccinimide which is substantially pure. It can also be used as a substitute for N-hydroxysuccinimide when the presence of water is not detrimental.

Accordingly, one embodiment of the invention is N-hydroxysuccinimide monohydrate.

Another embodiment of the invention is a method comprising: (a) dissolving solid N-hydroxysuccinimide in water to form a substantially salt-free aqueous solution; and (b) precipitating N-hydroxysuccinimide monohydrate from said solution.

A water-miscible organic cosolvent such as tetrahydrofuran [CAS 109-99-9] may be present in the aqueous solution, but it is preferred that the aqueous solution be free of organic cosolvent.

Precipitation of the N-hydroxysuccinimide monohydrate may be accomplished by cooling the aqueous solution and/or by evaporating water from the aqueous solution.

When water is evaporated from the aqueous solution, the temperature should be below the melting point of the N-hydroxysuccinimide monohydrate which is in the range of from 41° C. to 45° C.

When water is evaporated from the aqueous solution, the pressure at which evaporation is accomplished is susceptible to wide variation. In general, the pressure may be subatmospheric, ambient atmospheric, or superatmospheric. The rate of evaporation of water removal at a given temperature is enhanced by using subatmospheric pressures. Usually the pressure is in the range of from 0.1 to 101 kilopascals, absolute. Often the pressure is in the range of from 1 to 50 kilopascals, absolute. From 1 to 10 kilopascals, absolute, is preferred. For convenience, ambient atmospheric pressure is often used.

It has also been discovered that N-hydroxysuccinimide monohydrate can be produced from succinic anhydride and free hydroxylamine such that the product is substantially free of contaminating salt.

Accordingly, another embodiment of the invention is a method comprising: (a) reacting succinic anhydride with free hydroxylamine in water to form a substantially salt-free reaction mixture; (b) heating the reaction mixture and removing water to produce solid N-hydroxysuccinimide; (c) dissolving the solid N-hydroxysuccinimide in water to form a substantially salt-free aqueous solution; and (d) precipitating N-hydroxysuccinimide monohydrate from the solution.

The reaction of step (a) is conducted in the liquid phase.

Since free hydroxylamine rather than a salt of hydroxylamine is used, the product is substantially free of contaminating salt.

A water-miscible organic cosolvent such as tetrahydrofuran may be present in the reaction mixture, but it is preferred that the reaction mixture be free of organic cosolvent. Similarly, a water-miscible organic cosolvent such as tetrahydrofuran may be present in the aqueous solution, but it is preferred that the aqueous solution be free of organic cosolvent.

The temperature at which the reaction of step (a) is conducted may vary widely, but usually it is in the range of from 0° C. to 100° C. In many instances the temperature is in the range of from 0° C. to 80° C. From 10° C. to 60° C. is preferred.

Although it is not desired to be bound by any theory, it is believed that the reaction of step (a) produces several aliphatic species. It is also believed that water removal as well as heating is necessary in step (b) to achieve dehydration leading to cyclization and the production of N-hydroxysuccinimide, at least in good yields.

The temperature to which the reaction mixture is heated in step (b) may vary widely. The temperature should not be so high as to cause significant decomposition and/or discoloration of the product. Ordinarily the temperature is in the range of from 50° C. to 200° C. In many cases the temperature is in the range of from 70° C. to 150° C. From 90° C. to 120° C. is preferred.

The temperature at which water is removed from the reaction mixture in step (b) may also vary widely. Again, the temperature should not be so high as to cause significant decomposition and/or discoloration of the product. Usually the temperature is in the range of from 50° C. to 200° C. Frequently the temperature is in the range of from 70° C. to 150° C. From 90° C. to 120° C. is preferred.

The pressure at which water removal is accomplished in step (b) is also susceptible to wide variation. In general, the pressure may be subatmospheric, ambient atmospheric, or superatmospheric. The rate of water removal at a given temperature is enhanced by using subatmospheric pressures. Usually the pressure is in the range of from 0.1 to 101 kilopascals, absolute. Often the pressure is in the range of from 1 to 50 kilopascals, absolute. From 1 to 10 kilopascals, absolute, is preferred.

Water removal can also be enhanced by purging the reactor with an inert gas such as nitrogen during the heating.

Precipitation of the N-hydroxysuccinimide monohydrate from the aqueous solution in step (d) may be accomplished by cooling the aqueous solution and/or by evaporating water from the aqueous solution.

When water is evaporated from the aqueous solution to precipitate N-hydroxysuccinimide monohydrate, the temperature is preferably below the melting point of the N-hydroxysuccinimide monohydrate which is in the range of from 41° C. to 45° C.

When water is evaporated, the pressure may be varied in accordance with the principles of the preceding paragraph to vary the rate of water removal. Usually the pressure is in the range of from 0.1 to 101 kilopascals, absolute. Often the pressure is in the range of from 1 to 50 kilopascals, absolute. From 1 to 10 kilopascals, absolute, is preferred. For convenience ambient atmospheric pressure is often used.

N-hydroxysuccinimide monohydrate can be used in any application where the presence of water is not detrimental.

N-hydroxysuccinimide monohydrate can be also used to produce very pure anhydrous N-hydroxysuccinimide.

Accordingly, another embodiment is a method comprising removing water of hydration from N-hydroxysuccinimide monohydrate to produce anhydrous N-hydroxysuccinimide.

The water of hydration may be removed by heating the N-hydroxysuccinimide monohydrate. In most cases the water of hydration is removed at temperatures in the range of from 20° C. to 150° C. Often the temperature is in the range of from 60° C. to 120° C. From 90° C. to 120° C. is preferred.

The pressure at which the water of hydration is removed may be subatmospheric, ambient atmospheric, or superatmospheric. Usually the pressure is subatmospheric. Frequently the pressure is in the range of from 0.1 to 101 kilopascals, absolute. Often the pressure is in the range of from 1 to 50 kilopascals, absolute. From 1 to 10 kilopascals, absolute, is preferred.

The invention is further described in conjunction with the following examples which are to be considered illustrative rather than limiting, and in which all parts are parts by weight and all percentages are percentages by weight unless otherwise specified.

EXAMPLE 1

One hundred thirty-two grams of a 50 percent aqueous solution of free hydroxylamine was diluted with 70.0 milliliters of water in a flask and cooled in a water bath to 20° C. Two hundred grams of succinic anhydride was added in 4 installments with stirring, keeping the temperature below 40° C. After the addition had been completed, a vacuum was applied to reduce the pressure to about 16 kilopascals, absolute and the reaction mixture was heated to distill out water. As the temperature rose, the pressure was gradually further reduced until the pressure was about 13 kilopascals, absolute, at a temperature of 105° C. These conditions were maintained for 2 hours. The reaction mixture was then cooled to 80° C. and 100 milliliters of water was added. The solution was then cooled with stirring to 20° C. and a few crystals of N-hydroxysuccinimide was added. Cooling with stirring was continued until a temperature of 5° C. was reached. Stirring was then discontinued and the reaction mixture was allowed to stand quiescently overnight. The next day the crystals that had precipitated were removed by filtration and washed once with about 30 milliliters of acetone. Drying yielded 145.0 grams of white crystals. Nuclear magnetic resonance spectroscopy showed the crystals to be N-hydroxysuccinimide monohydrate. Thermogravimetric analysis showed a 12.4 percent weight loss on heating, thereby indicating the product to be a monohydrate.

The filtrate was stripped in vacuo to remove all solvent. The yellow oily residue weighed 110.0 grams and solidified slowly on cooling. A clear solution was obtained by heating 74.5 grams of the solidified residue with 20 milliliters of water. The solution was cooled initially to ambient room temperature. A few seed crystals of N-hydroxysuccinimide monohydrate was added and the mixture was allowed to stand quiescently in a refrigerator overnight. The crystals which precipitated were removed by filtration, washed with cold acetone and dried. The weight of this second crop of N-hydroxysuccinimide monohydrate crystals was 34.0 grams.

EXAMPLE 2

One hundred thirty-two grams of a 50 percent aqueous solution of free hydroxylamine was diluted with 70.0 milliliters of water in a flask and cooled in a water bath to 20° C. Two hundred grams of succinic anhydride was added in 4 installments with stirring, keeping the temperature below 40° C. After the addition had been completed, a vacuum was applied to reduce the pressure to about 16 kilopascals, absolute and the reaction mixture was heated to distill out water. As the temperature began to rise, the pressure was gradually further reduced until the pressure was about 13 kilopascals, absolute, at a temperature of 105° C. These conditions were maintained for 2 hours. The reaction mixture was then cooled to 80° C. and 125 milliliters of water was added. The reaction mixture was cooled in an ice-acetone bath to –5° C. with stirring to precipitate crystals. After half an hour the crystals were broken up and filtered under suction. The crystals were then washed with acetone and dried. The dried crystals of N-hydroxysuccinimide monohydrate weighed 151 grams.

The mother liquor was concentrated to 100 grams in vacuo and seeded with a few crystals of N-hydroxysuccinimide monohydrate and allowed to stand quiescently in a refrigerator overnight. The mother liquor was decanted from the crystals which had precipitated, The crystals were washed with acetone and dried. The dried crystals weighed 45.0 grams. These crystals were redissolved in 25 milliliters of warm water. The resulting solution was decolorized with charcoal and filtered. The filtrate was seeded with a few crystals from the first crop, cooled to 0° C., and maintained at 0° C. for 18 hours. The crystals which precipitated were filtered, washed, and dried. The dried crystals of N-hydroxysuccinimide monohydrate weighed 20.0 grams. These crystals were recrystallized from 10 milliliters of water, washed with acetone, and dried. The dried crystals of N-hydroxysuccinimide monohydrate weighed 10.0 grams and had a melting range of from 42° C.–45° C. The water content was 13 percent as determined by the Karl Fischer method, thereby indicating the product to be a monohydrate.

EXAMPLE 3

A 50 percent aqueous hydroxylamine solution in the amount of 132.0 grams was diluted with 70 milliliters of water. The diluted solution was charged to a reactor equipped with a mechanical stirrer, a temperature controller, and a distillation assembly. The solution was stirred and 200 grams of succinic anhydride was added in 4 installments. The temperature of the reaction mixture rose to a maximum of 86° C. The reactor was gradually evacuated to distill water. Upon applying the vacuum, the temperature first dropped and then rose. As the temperature began to rise, the absolute pressure was slowly decreased. The reaction mixture was gradually heated to 115° C. and the pressure was decreased to 1.3 kilopascals, absolute. These conditions were maintained for ½ hour. The vacuum was released under nitrogen and the reaction mixture was cooled to 80° C. One hundred thirty milliliters of water was added and the reaction mixture was cooled with stirring to −4° C. and stirred at this temperature for ½ hour. The crystals that precipitated were filtered out under suction and dried in air to obtain 163 grams of crystals. The crystals melted in the range of 41° C.–44° C. The melting range is indicative that the crystals were N-hydroxysuccinimide monohydrate.

One hundred grams of the above crystals were placed in a 250-milliliter reaction flask which was attached to a rotary evaporator. A vacuum was applied until the pressure was about 2 kilopascals, absolute. While maintaining the vacuum, the crystals were heated and maintained at temperatures in the range of from 80° C. to 90° C. for 2 hours. The pressure was then reduced to about 0.3 kilopascal, absolute, using a high vacuum pump and maintained at that pressure for ½ hour. The resulting product weighed 86.0 grams and melted in the range of 95° C.–98° C. Both the weight and the melting range are indicative that the product was anhydrous N-hydroxysuccinimide.

Although the present invention has been described with reference to specific details of certain embodiments thereof, it is not intended that such details should be regarded as limitations upon the scope of the invention except insofar as they are included in the accompanying claims.

I claim:

1. N-Hydroxysuccinimide monohydrate.

2. A method comprising:
   (a) dissolving solid N-hydroxysuccinimide in water to form a substantially salt-free aqueous solution; and
   (b) precipitating N-hydroxysuccinimide monohydrate from said solution.

3. The method of claim 2 wherein said aqueous solution is free of organic cosolvent.

4. The method of claim 2 wherein said aqueous solution is cooled to precipitate said N-hydroxysuccinimide monohydrate.

5. The method of claim 2 wherein water is evaporated from said aqueous solution to precipitate said N-hydroxysuccinimide monohydrate.

6. The method of claim 5 wherein said water is evaporated from said aqueous solution under ambient atmospheric pressure.

7. The method of claim 5 wherein said water is evaporated from said aqueous solution under subatmospheric pressure.

8. The method of claim 7 wherein said subatmospheric pressure is in the range of from 0.1 to 101 kilopascals, absolute.

9. A method comprising:
   (a) reacting succinic anhydride with free hydroxylamine in water to form a substantially salt-free reaction mixture;
   (b) heating said reaction mixture and removing water to produce solid N-hydroxysuccinimide;
   (c) dissolving said solid N-hydroxysuccinimide in water to form a substantially salt-free aqueous solution; and
   (d) precipitating N-hydroxysuccinimide monohydrate from said solution.

10. The method of claim 9 wherein said reaction mixture is free of organic cosolvent.

11. The method of claim 9 wherein the reaction of step (a) is conducted at temperatures in the range of from 0° C. to 100° C.

12. The method of claim 9 wherein said reaction mixture is heated to temperatures in the range of from 50° C. to 200° C.

13. The method of claim 9 wherein said water is removed from said reaction mixture at temperatures in the range of from 50° C. to 200° C.

14. The method of claim 9 wherein said water is removed from said reaction mixture under ambient atmospheric pressure.

15. The method of claim 9 wherein said water is removed from said reaction mixture under subatmospheric pressure.

16. The method of claim 14 wherein said subatmospheric pressure is in the range of from 0.1 to 101 kilopascals, absolute.

17. The method of claim 9 wherein said aqueous solution is free of organic cosolvent.

18. The method of claim 9 wherein said aqueous solution is cooled to precipitate said N-hydroxysuccinimide monohydrate.

19. The method of claim 9 wherein water is evaporated from said aqueous solution to precipitate said N-hydroxysuccinimide monohydrate.

20. The method of claim 19 wherein said water is evaporated from said aqueous solution under ambient atmospheric pressure.

21. The method of claim 19 wherein said water is evaporated from said aqueous solution under subatmospheric pressure.

22. The method of claim 21 wherein said subatmospheric pressure is in the range of from 0.1 to 101 kilopascals, absolute.

23. A method comprising removing water of hydration from N-hydroxysuccinimide monohydrate to produce anhydrous N-hydroxysuccinimide.

24. The method of claim 23 wherein the removal of said water of hydration is accomplished by heating said N-hydroxysuccinimide monohydrate.

25. The method of claim 23 wherein said water of hydration is removed at temperatures in the range of from 20° C. to 150° C.

26. The method of claim 23 wherein said water of hydration is removed under subatmospheric pressure.

27. The method of claim 26 wherein said subatmospheric pressure is in the range of from 0.1 to 101 kilopascals, absolute.

* * * * *